Figure 1:
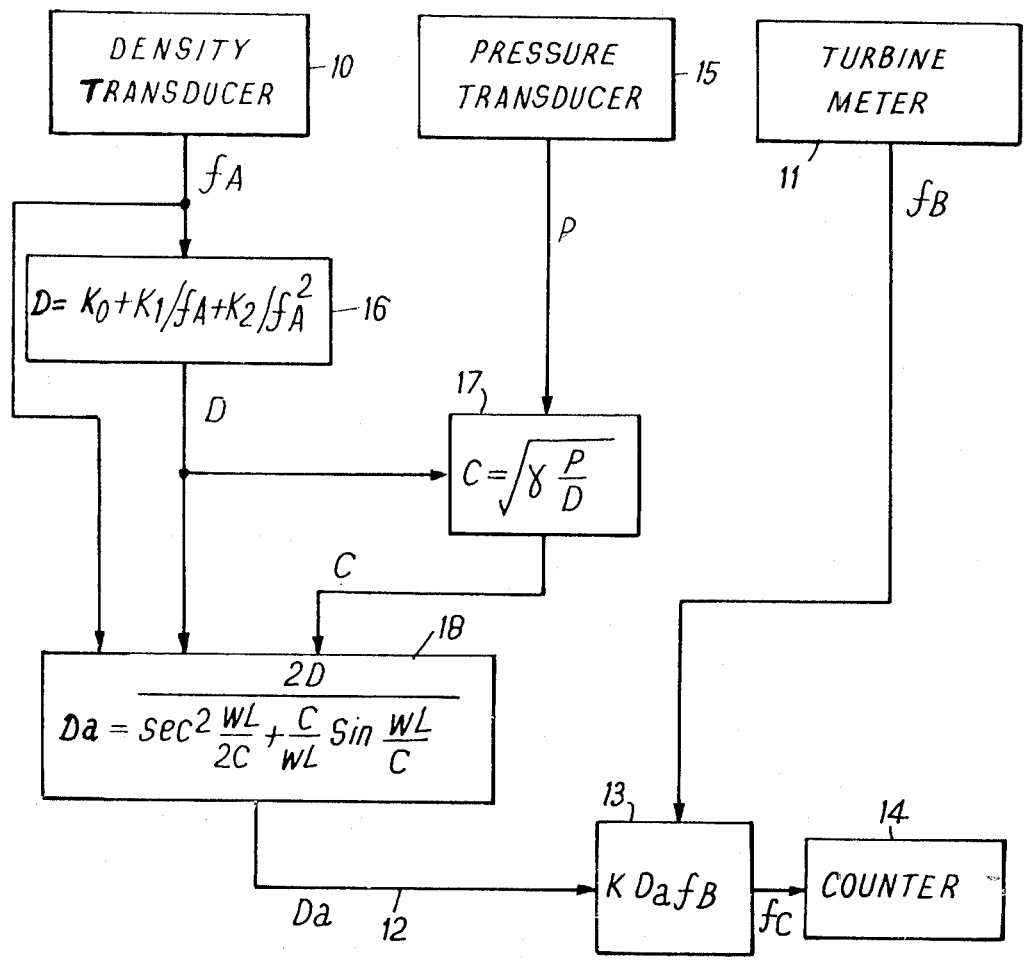

United States Patent [19]

Stansfeld

[11] 4,262,523
[45] Apr. 21, 1981

[54] MEASUREMENT OF FLUID DENSITY

[75] Inventor: James W. Stansfeld, Beech, near Alton, England

[73] Assignee: The Solartron Electronic Group Limited, Farnborough-Hampshire, England

[21] Appl. No.: 962,864

[22] Filed: Nov. 22, 1978

[30] Foreign Application Priority Data

Dec. 9, 1977 [GB] United Kingdom ............... 51409/77

[51] Int. Cl.$^3$ ................................................ G01N 9/00
[52] U.S. Cl. ...................................... 73/30; 73/32 A; 73/861.11
[58] Field of Search ............................ 73/30, 32 A, 24

[56] References Cited

U.S. PATENT DOCUMENTS

3,874,221  4/1975  Deverill ................................. 73/30

FOREIGN PATENT DOCUMENTS

1126450  9/1968  United Kingdom ..................... 73/32 A

OTHER PUBLICATIONS

Potter, P.N., Sound Velocity Effect on Vibrating Cylinder Density Transducers, a Publication of the Solartron Electronic Group Ltd. Farnborough, Hampshire, England, no date given but cited in U.S. Pat. No. 3,874,221.

*Primary Examiner*—S. Clement Swisher
*Attorney, Agent, or Firm*—Joseph J. Kaliko; Mikio Ishimaru; Dale V. Gaudier

[57] ABSTRACT

A vibrating fluid density transducer 10 provides a gas density measurement D, used in conjunction with a flowmeter signal $f_B$ to meter the mass of gas fed through a pipeline. D is subject to errors dependent upon the velocity of sound C in the gas. The errors are corrected to yield Da by application of a correcting formula (block 18) in which C is introduced by calculation (block 17) from a measurement of gas pressure P by a transducer P. The value of C may alternatively be measured directly, computed from a measurement of specific gravity or in the case of a liquid, be inferred from D or be preset.

18 Claims, 2 Drawing Figures

MEASUREMENT OF FLUID DENSITY

The present invention is concerned with the measurement of fluid density utilising a vibrating fluid density transducer, that is to say a transducer which incorporates a resonantly vibratable sensing element arranged, in operation, to be resonantly vibrated while at least partially exposed to the fluid whose density is to be sensed, the frequency of vibration being dependent upon the density of the fluid. The density is determined from the measured frequency in accordance with a known formula such as the formula:

$$D = K_0 + K_1/f_A + K_2/f_A^2 \qquad (1)$$

where
D is the density,
$K_0$, $K_1$ and $K_2$ are constants, and
$f_A$ is the measurement frequency.

An example of a vibrating fluid density transducer is described in U.S. Pat. No. 3,516,283, assigned to the same assignee as the present application. The sensing element may be a cylinder or tube. The transducer may measure gas density or liquid density.

One important use of a gas density transducer is in combination with a flowmeter to measure the mass of gas flowing through a pipeline. The mass is given by integrating the flow rate multiplied by the density. The mass may be used to determine the cost of fuel gas supplied to a Gas Board or other large-scale user on a formula involving the mass of gas and its calorific value. If the density measurement is in error, the cost is also in error and, in view of the large quantities of gas involved, even a small percentage error can lead to a large difference in cost.

It has been found that the density of a gas as measured by a vibrating fluid transducer is affected by the velocity of sound in the gas. In practical terms the density measurement may be up to 0.3% in error for natural gas and more for some special gases such as propane/air mix. This small percentage error can be significant in monetary terms. A velocity of sound error also occurs in a vibrating liquid density transducer, such as that disclosed in U.S. Pat. No. 3,444,723, also assigned to the same assignee as the present application.

The object of the present invention is to provide a fluid density measuring apparatus and method which enable the accuracy of measurement to be substantially improved.

According to the invention in one aspect there is provided a fluid density measuring apparatus, comprising a vibrating fluid density transducer providing, in operation, a first signal whose frequency is dependent upon the density of the fluid, means providing, in operation, a second signal dependent upon the velocity of sound in the fluid, and computing means responsive to the two signals to compute the density of the fluid from the first signal in accordance with a formula characteristic of the density transducer, subject to a non-linear correction dependent upon the second signal and such as to improve the accuracy of the density measurement.

As will be explained below, the necessary computations involve arithmetical steps and the computing means can be analog or digital computing means constructed to perform these steps or a digital computer programmed to perform these steps. In other words, the computing operations can be implemented in terms of hardware or software. The most accurate computations, however, involve trigonometrical functions and are therefore most readily implemented in terms of software.

The means which provide the second signal can be means which measure the velocity of sound in the fluid, e.g. utilising an ultrasonic transducer. In the case of a gas, the second signal can be provided by a pressure transducer, such as is described in U.S. Pat. No. 3,021,711 for example, although a simpler, less expensive pressure transducer would be satisfactory. The velocity of sound can be determined from the gas pressure as explained below.

Alternatively, the second signal can be provided by a specific gravity transducer, such as is described in U.S. Pat. No. 3,916,672, assigned to the same assignee as the present application for example. Again the velocity of sound can be determined from the gas specific gravity, (which, as indicated in the aforementioned U.S. Pat. No. 3,916,672, is given by $\rho g/\rho a$, where $\rho g$ and $\rho a$ are the respective densities of the gas and air, both at Standard Temperature and Pressure (STP), preferably with correction for temperature sensed by a further transducer.

In the case of a liquid the means which provide the second signal can derive a velocity of sound signal from the indicated density or provide a preset velocity of sound signal.

According to the invention in a second aspect, there is provided a method of measuring the density of a fluid wherein the measurement is made from a first signal provided by means of a vibrating fluid density transducer and is subjected to a non-linear correction in dependence upon a signal dependent upon the velocity of sound in the fluid, such that the accuracy of the density measurement is improved.

Dealing specifically with the measurement of gas density, as already explained the primary density measurement may be made by application of a formula such as $$D = K_0 + K_1/f_A + K_2/f_A^2 \qquad (1)$$

The value of D thus calculated, referred to as the indicated density, requires correction to provide the actual density $D_a$. It can be shown that the relationship between these two quantities is:

$$D = \tfrac{1}{2} D_a \left[ \sec^2 \frac{WL}{2C} + \frac{C}{WL} \sin \frac{WL}{C} \right] \qquad (2)$$

where
$W = 2\pi f_A$,
L is the length of the vibrating sensing element, and
C is the velocity of sound in the measured gas.

The correction may be performed by direct application of equation (2) or by application of an approximation to equation (2) such as:

$$D = D_a \left[ 1 + \tfrac{1}{6} \left( \frac{WL}{2C} \right)^2 \right] \qquad (3)$$

The quantities required to apply either equation are W which is known from the density transducer, L which may be introduced as a known constant, and C which has to be determined from a second transducer.

The velocity of sound C in gases at moderate pressure is given by:

$$C = \sqrt{\gamma \frac{P}{D}} \tag{4}$$

or even better by:

$$C = \sqrt{\gamma \frac{P}{D} + KD + K_2D^2 + K_3O^3 + K_4D^4} \tag{4a}$$

where each

K is a constant, $\gamma$ is the ratio of specific heats, i.e. $\gamma = C_p/C_v$, $C_p$ is specific heat at constant pressure and $C_v$ is specific heat at constant volume, and P is the gas pressure.

$\gamma$ may be taken to be a known constant. P can be measured by a pressure transducer. It is then possible to utilise equation (4) or (4a) to determine C which is then used in equation (2) or equation (3) to determine $D_a$ from D. The error introduced by using D rather than $D_a$ in equation (4) is negligible.

Naturally, the computation does not have to proceed via equation (4) and then equation (2) or equation (3). For example, equations (3) and (4) can be combined to yield:

$$D = D_a + D_a^2 \left[ \frac{W^2L^2}{24P} \right] \tag{5}$$

Thus we have a single quadratic equation to solve for $D_a$ in terms of the measured values of W and P and the computed value of D. Other equivalent algebraic procedures are obviously possible.

Equation (4) may alternatively be written as:

$$C = \sqrt{\gamma \frac{RT}{M}} \tag{6}$$

where

R is the gas constant,

T is absolute temperature, and

M is the molecular weight of the gas.

Since the molecular weight of a gas is proportional to its specific gravity, equation (6) may be written as:

$$C = \sqrt{\gamma \frac{RT}{AG}} \tag{7}$$

where

A is a constant, and

G is the specific gravity of the gas. It is therefore possible to use equation (7) in conjunction with equation (2) or (3), the value of G being measured by a specific gravity transducer. R and A are constants, $\gamma$ may be taken to be a constant and in many circumstances T may also be taken to be a constant. If necessary, T can be measured by a third transducer.

Again it is possible to combine equations. If equations (3) and (7) are combined, we have:

$$D = D_a[1 + (W^2L^2AG)]/24\gamma RT \tag{8}$$

Turning now to a liquid density measurement, a suitable correction formula is:

$$D_a = D(1 - Kf_A^2/C^2) \tag{9}$$

where K is a constant determined primarily by the characteristics of the transducer. The velocity of sound C can be measured directly with an acoustic transducer, e.g. of the ultrasonic type, or inferred from the indicated density D using the formula:

$$C = \sqrt{D/B} \tag{10}$$

where B is the adiabatic compressibility of the liquid. B can be assumed to be constant over a limited temperature range. It is also possible to assume C to be a constant, if the density measurement is made within a restricted temperature range. In fact the velocity of sound in a liquid is markedly dependent upon temperature but, since C is large in a liquid, the correcting term $Kf_A/C^2$ is small and a useful improvement is possible with C assumed constant (over a limited temperature range).

Two embodiments of the invention will now be described by way of example with reference to FIGS. 1 and 2 of the accompanying drawings, which are partially block and partially flow diagrams illustrating the computational steps which may readily be performed by a suitably programmed general purpose computer or a suitably constructed special purpose computer. The preferred implementation is by way of a microprocesser.

In both Figures, a known vibrating gas density transducer 10 provides a signal of frequency $f_A$ and a known turbine flowmeter 11 provides a signal of frequency $f_B$ representing volume flow rate. The actual density $D_a$ is represented on a line 12 and a binary rate multiplier 13 multiplies the frequency $f_B$ by $KD_a$, where K is a constant, to provide a frequency $f_C$ representing mass flow rate. The signal at $f_C$ is applied to a counter 14 which integrates the mass flow rate to provide an integration of the total mass of gas metered through the flowmeter 11.

A known pressure transducer 15 provides a signal P representing gas pressure; this signal may be a current ranging over the range 4 to 20 mA.

The computations to determine $D_a$ are performed in FIG. 1 as follows. Block 16 operates upon $f_A$ to provide D in accordance with equation (1). Block 17 operates upon P and D to provide C in accordance with equation (4). Block 18 operates upon D, C and $f_A$ to provide $D_a$ in accordance with equation (2) but could be simplified to operate on the basis of equation (3).

Figure 2:
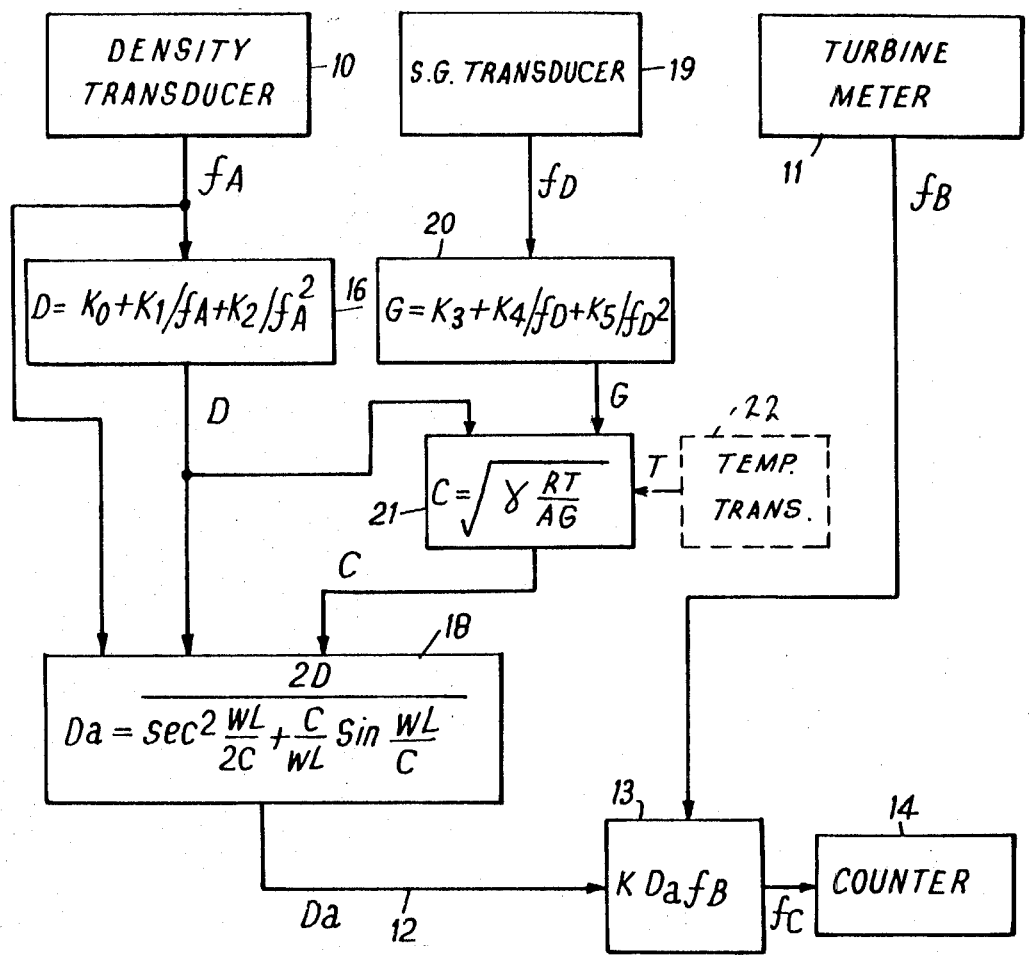

In FIG. 2, the pressure transducer 15 is replaced by a specific gravity transducer 19 providing an output frequency $f_D$. Block 20 computes G in accordance with the equation:

$$G = K_3 + K_4/f_D + K_5/f_D^2 \tag{9}$$

where $K_3$, $K_4$ and $K_5$ are constants characteristic of the transducer 19.

As will be apparent from the aforementioned U.S. Pat. No. 3,916,672, the specific gravity transducer described therein is based upon a vibrating fluid density transducer and therefore equation (9) has the same form as equation (1). Block 17 of FIG. 1 is replaced by block 21 in FIG. 2, which calculates C in accordance with equation (7). An optional third transducer 22 is shown for measuring T when this cannot be regarded as a constant.

For extreme accuracy the variation of $\gamma$ can be taken into account. For example, the variation of $\gamma$ may be related approximately to the variation of P/D and this makes it possible, without any further measurements, to apply a small correcting term to $\gamma$ in block 17, calculated from P/D.

In an alternative embodiment, the signal C in FIG. 1 could be provided directly by means measuring the velocity of sound in the fluid, this alternative being also applicable to liquid density measurement, subject to appropriate rewriting of the equations in blocks 16 and 18. For liquid density measurement, the value of C could be entered manually into block 18.

I claim:

1. A fluid density measuring apparatus, comprising a vibrating fluid density transducer providing, in operation, a first signal whose frequency is dependent upon the density of the fluid, means providing, in operation, a second signal dependent upon the velocity of sound in the fluid, wherein the means providing the second signal are means which measure the velocity of sound in the fluid, and computing means responsive to the two signals to compute the density of the fluid from the first signal in accordance with a formula characteristic of the density transducer, subject to a non-linear correction dependent upon the second signal and such as to improve the accuracy of the density measurement.

2. A gas density measuring apparatus, comprising a vibrating gas density transducer providing, in operation, a first signal whose frequency is dependent upon the density of the gas, means providing, in operation, a second signal dependent upon the velocity of sound in the gas, wherein the means providing the second signal are means which measure the pressure of the gas and means which compute the velocity of sound from the pressure, and computing means responsive to the two signals to compute the density of the gas from the first signal in accordance with a formula characteristic of the density transducer, subject to a non-linear correction dependent upon the second signal and such as to improve the accuracy of the density measurement.

3. A gas density measuring apparatus, comprising a vibrating gas density transducer providing, in operation, a first signal whose frequency is dependent upon the density of the gas, means providing, in operation, a second signal dependent upon the velocity of sound in the gas, wherein the means providing the second signal are means which measure the specific gravity of the gas and further means which complete the velocity of sound from the specific gravity, and computing means responsive to the two signals to compute the density of the gas from the first signal in accordance with a formula characteristic of the density transducer, subject to a non-linear correction dependent upon the second signal and such as to improve the accuracy of the density measurement.

4. Apparatus according to claim 3, further comprising a temperature transducer and wherein the said further means correct the computed velocity of sound from the measured temperature.

5. A method of measuring the density of a fluid wherein the measurement is made from a first signal provided by means of a vibrating fluid density transducer and is subjected to a non-linear correction in dependence upon a second signal representative of another sensed parameter of the fluid, said other parameter being dependent upon the velocity of sound in the fluid, such that the accuracy of the density measurement is improved.

6. A method according to claim 5, wherein the fluid is a gas and the correction is performed in accordance with equation (2) above or an approximation thereto.

7. A method according to claim 6, wherein the value of C in equation (2) is determined from the gas pressure.

8. A method according to claim 6, wherein the value of C in equation (2) is determined from the gas specific gravity.

9. Fluid density measuring apparatus, comprising:
a vibrating fluid density transducer for producing a first signal whose frequency is dependent upon the density of the fluid;
at least one further transducer for producing a second signal which is representative of another parameter of the fluid, said other parameter being selected to be functionally related to the velocity of sound in the fluid; and
computing means for correcting the density measurement represented by the first signal in dependence upon the second signal to improve the accuracy of the density measurement.

10. Apparatus as claimed in claim 9, wherein said further transducer comprises a transducer for sensing the velocity of sound in the fluid and for producing said second signal in dependence thereupon.

11. Apparatus as claimed in claim 9, for gas density measurement, wherein said further transducer comprises a pressure transducer for sensing the pressure of the gas and for producing said second signal in dependence thereupon.

12. Apparatus as claimed in claim 9, for gas density measurement, wherein said further transducer comprises a specific gravity transducer for sensing the specific gravity of the gas and for producing said second signal in dependence thereupon.

13. Apparatus as claimed in claim 12, further comprising a third transducer for producing a third signal dependent upon the temperature of the gas, the computing means being arranged to effect said correction in dependence upon both the second signal and the third signal.

14. A method of measuring the density of a fluid, the method comprising the steps of:
(a) sensing the density of the fluid using a vibrating fluid density transducer, to produce a first signal whose frequency is dependent of the density of the fluid;
(b) sensing another parameter of the fluid, said other parameter being selected to be functionally related to the velocity of sound in the fluid, to produce a second signal which is representative of said other parameter; and
(c) combining said first and second signals so as to correct the density measurement represented by said first signal in dependence upon the second signal, to improve the accuracy of the density measurement.

15. A method as claimed in claim 14, wherein said step (b) comprises sensing the velocity of sound in the fluid.

16. A method as claimed in claim 14, for gas density measurement, wherein said step (b) comprises sensing the pressure of the gas.

17. A method as claimed in claim 14, for gas density measurement, wherein said step (b) comprises sensing the specific gravity of the gas.

18. A method as claimed in claim 17, further including the step of sensing the temperature of the gas to produce a third signal which is representative thereof, said step (c) including combining said third signal with said first and second signals to enhance said correction.

* * * * *